(12) United States Patent
Nelson

(10) Patent No.: US 8,759,398 B2
(45) Date of Patent: Jun. 24, 2014

(54) PHOSPHORUS BINDER COMPOSITION FOR TREATMENT OF HYPERPHOSPHATEMIA

(71) Applicant: Biolink Life Sciences, Inc., Cary, NC (US)

(72) Inventor: Deanna J. Nelson, Raleigh, NC (US)

(73) Assignee: Biolink Life Sciences, Inc., Cary, NC (US)

( * ) Notice: Subject to any disclaimer, the term of this patent is extended or adjusted under 35 U.S.C. 154(b) by 0 days.

(21) Appl. No.: 13/935,136

(22) Filed: Jul. 3, 2013

(65) Prior Publication Data

US 2013/0296433 A1 Nov. 7, 2013

Related U.S. Application Data

(63) Continuation-in-part of application No. 13/097,141, filed on Apr. 29, 2011.

(60) Provisional application No. 61/330,610, filed on May 3, 2010.

(51) Int. Cl.
*A61K 31/194* (2006.01)
*A61K 33/06* (2006.01)
*A61K 31/08* (2006.01)

(52) U.S. Cl.
CPC ............... *A61K 31/194* (2013.01); *A61K 31/08* (2013.01); *A61K 33/06* (2013.01); *A23V 2250/1578* (2013.01)
USPC ............................. 514/574; 514/53; 514/711

(58) Field of Classification Search
CPC ............... A61K 31/194; A61K 33/06; A23V 2250/1578
USPC .............................................. 514/574, 53, 711
See application file for complete search history.

(56) References Cited

U.S. PATENT DOCUMENTS

| | | | |
|---|---|---|---|
| 6,752,953 B2 * | 6/2004 | Chen et al. | 264/330 |
| 2006/0228424 A1 * | 10/2006 | Nelson | 424/617 |
| 2008/0260682 A1 * | 10/2008 | Rose et al. | 424/78.38 |
| 2009/0269399 A1 * | 10/2009 | Lewis et al. | 424/452 |

FOREIGN PATENT DOCUMENTS

WO WO02/34069 * 5/2002

* cited by examiner

*Primary Examiner* — Bong-Sook Baek
(74) *Attorney, Agent, or Firm* — Casimir Jones SC

(57) ABSTRACT

The present invention relates to oral pharmaceutical products which are useful for binding phosphorus in ingesta, and inhibiting absorption of phosphorus from the gastrointestinal tract of subjects. A method for binding phosphorus in ingesta and inhibiting its absorption from the gastrointestinal tract is also provided. The pharmaceutical products and methods of the present invention are particularly useful in the treatment of hyperphosphatemia of chronic uremia and reducing serum phosphorus levels in patients requiring such therapy.

2 Claims, 2 Drawing Sheets

PHOSPHORUS BINDER COMPOSITION FOR TREATMENT OF HYPERPHOSPHATEMIA

FIELD OF THE INVENTION

The present invention relates to oral pharmaceutical products which are useful for binding phosphorus in ingesta, and inhibiting absorption of phosphorus from the gastrointestinal tract. A method for binding phosphorus in ingesta and inhibiting its absorption from the gastrointestinal tract is also provided. The pharmaceutical products and methods of the present invention are useful in the treatment of hyperphosphatemia and reducing serum phosphorus levels in patients requiring such therapy.

BACKGROUND OF THE INVENTION

In the adult human, normal serum phosphorus levels range from 2.5 to 4.5 mg/dL (0.81 to 1.45 mmol phosphorus/L). (Normal serum levels are typically 50% higher in infants and 30% higher in children due to growth hormone effects.) Hyperphosphatemia is a disease state in which there is an abnormally elevated serum phosphorus (Pi) level in the serum. Significant hyperphosphatemia is considered present when serum phosphorus levels are greater than about 5 mg/dL in adults or 7 mg/dL in children or adolescents. [National Kidney Foundation. Am J Kidney Dis 2003; 42 (Suppl 3):S1-S201.]

The kidney plays a central role in maintaining a condition of phosphorus homeostasis in the body of a subject, wherein the amount of phosphorus absorbed from the gastrointestinal tract approximately equals the amount excreted via the kidney. In addition, cellular release of phosphorus is balanced by uptake in other tissues. Hormonal control is provided by parathyroid hormone.

Since the kidney plays a central role in maintaining phosphorus homeostasis, kidney dysfunction is often accompanied by increased phosphorus retention by the body. In early kidney dysfunction, compensatory physiological responses allow for a continued match between urinary phosphorus excretion and phosphorus absorption from the gastrointestinal (GI) tract, and serum phosphorus levels remain near normal values. With more advanced renal failure, however, elevated serum phosphorus is a predictable co-morbidity.

In patients with chronic kidney disease (CKD), phosphorus retention (as evidenced by abnormally elevated serum phosphorus levels) may contribute to progression of renal failure and is a major factor in the development of secondary hyperparathyroidism, renal osteodystrophy, and soft tissue calcification. [Tonelli M, Pannu N, Manns B. Oral phosphate binders in patients with kidney failure. New England J Med 2010; 362: 1312-1324.] Hyperphosphatemia in CKD patients is treated by restriction of phosphorus in the diet and pharmacological means. Serum phosphorus is also reduced during dialysis of end-stage renal disease patients undergoing such treatment.

Phosphorus is present in nearly all foods, and absorption of dietary phosphorus from ingesta in the gastrointestinal (GI) tract is very efficient. Normal daily dietary intake varies from 800-1,500 mg of phosphorus. Typically, 70-90% of dietary phosphorus is absorbed, primarily from the jejunum, duodenum, and proximal ileum of the GI tract, although some absorption continues throughout the remainder of the intestinal tract. A small amount of GI excretion occurs.

The efficient absorption of phosphorus from food and the need to provide a diet sufficient to counter the catabolic state of CKD render dietary restriction insufficient to prevent hyperphosphatemia. Moreover, conventional dialysis fails to reduce levels of phosphorus in the blood, and serum phosphorus levels increase with time. Therefore, prevention of phosphorus absorption with pharmacological means is generally required to prevent or reverse hyperphosphatemia and the morbidities and mortality risks associated with it.

Methods for the prevention and treatment of hyperphosphatemia include the use of compounds or compositions that will bind phosphorus in the gastrointestinal (GI) tract of a subject and prevent its absorption into the systemic circulation. Compounds that bind phosphorus in the GI tract are known as phosphorus (Pi) binders. Today, oral phosphate binders are used in over 90% of patients with kidney failure and/or hyperphosphatemia, at an annual cost of approximately $750 million (U.S. dollars) worldwide.

Phosphorous binding is a chemical reaction between dietary phosphorus and a cation of a binder compound. Chemical reaction results in the formation of insoluble and hence unabsorbable phosphate compounds, adsorption of phosphorus-containing anions on the surface of binder particles, or a combination of both processes.

Metal salts comprise the most clinically important class of phosphorus binders and are ingested to bind dietary phosphate and convert it to insoluble phosphate salts, thus preventing its absorption from the GI tract. Known metal salts with phosphate-binding properties are aluminum hydroxide and aluminum carbonate; calcium acetate, calcium carbonate, calcium citrate, calcium alginate, calcium gluconate, calcium lactate, and calcium sulfate; lanthanum carbonate and lanthanum carbonate hydrates; magnesium carbonate and magnesium hydroxide; as well as complex salts of iron. (Not all of these salts have gained therapeutic importance or been considered safe or efficacious for Pi binding.) Polymeric materials having a plurality of cationic sites (e.g., tertiary and quaternary amines) appended thereto constitute the second clinically important class of phosphorus binders.

Phosphorus binding by metal salts is affected by the pH of the solution environment. The solution pH affects both the rate of dissolution of the metal salt and the subsequent binding reaction between the metal ion and phosphate. In general, an acidic pH is best to dissolve and ionize the salt, but reaction of the metal with the phosphate and precipitation of metal phosphate from solution is optimal at higher values of pH.

Of the metal salts listed above, calcium salts constitute the group of phosphate binders used most extensively by patients worldwide to control serum Pi levels (Table 1).

TABLE 1

Calcium salts that have been studied as Pi binders

| Calcium Source | % Ca, by weight | Remarks |
|---|---|---|
| Calcium Carbonate | 40% | Wide variations in ionized Ca bioavailability and trace metal contamination; widely used outside the U.S. for Pi binding |
| Calcium Acetate | 23% | Regurgitation of acetic acid (vinegar breath) is a significant side effect. Only calcium acetate has been approved by the U.S. Food and Drug Administration for clinical use as a phosphate binder. |
| Calcium Citrate | 21% | Enhances absorption of calcium and other metals from the gut, including (adventitious) dietary aluminum. |
| Calcium Formate | 31% | Chronic absorption of formate is reported to cause albuminuria and hematuria. Pungent odor. Skin irritant. |

TABLE 1-continued

Calcium salts that have been studied as Pi binders

| Calcium Source | % Ca, by weight | Remarks |
|---|---|---|
| Calcium Lactate | 14% | Used as a dietary supplement, not as a Pi binder. |
| Calcium Gluconate | 9% | Used as a dietary supplement, not as a Pi binder. |

In U.S. Pat. No. 4,889,725 Veltman discloses a means for promoting the neutralization reaction between particulate calcium carbonate and ionized phosphate by adding a material formed by the reaction of particulate calcium carbonate and dilute hydrofluoric acid. The products of this invention are useful in lowering serum phosphorus levels in patients undergoing renal dialysis, and are also useful as antacids.

A common treatment for controlling Pi levels is disclosed in U.S. Pat. No. 4,870,105 to Fordtran, which discloses a calcium acetate phosphorus binder for oral administration to an individual for the purpose of inhibiting gastrointestinal absorption of phosphorus. It further discloses a method of inhibiting gastrointestinal absorption of phosphorus, comprising administering orally the calcium acetate phosphorus binder, preferably close in time to food and beverage consumption. Likewise, U.S. Pat. No. 6,576,665 to Dennett, Jr. et al. discloses a composition for inhibiting gastrointestinal absorption of phosphorus in an individual. The composition includes a quantity of calcium acetate sufficient to bind the phosphorus and having a bulk density of between 0.50 kg/L and 0.80 kg/L and is dimensioned to form a caplet for fitting within a capsule. Further provided is a method for administering the calcium acetate composition. Likewise, U.S. Patent Application 2003/0050340 to Dennett, Jr., et al. discloses a composition for binding phosphorus within the gastrointestinal tract of an individual. The composition includes a quantity of calcium acetate having a specific bulk density sufficient to bind the phosphorus in the gastrointestinal tract of an individual. Further provided is a method for administering the calcium acetate composition.

U.S. Pat. No. 4,689,322, to Kulbe et al. provides calcium salts or calcium mixed salts of polymeric, anionic carboxylic acids and/or an ester of sulfuric acid, and methods for their preparation and use, discloses a pharmaceutical product which contains at least a calcium salt or a calcium mixed salt of a natural or chemically modified polymeric, anionic carboxylic acid and/or an ester of sulfuric acid, and additive materials and/or carrier materials. There are further disclosed calcium salts, and methods of preparation thereof, comprised of polymannuronic acid, polygalacturonic acid, polyglucuronic acid, polyguluronic acid, the oxidation products of homoglycans, the oxidation products of heteroglycans, or their mixtures, for controlling the levels of phosphorus, calcium and iron in patients with chronic uremia and/or the control of the oxalate and/or phosphate of the blood in kidney stone prophylaxis.

U.S. Pat. Nos. 6,160,016 and 6,489,361 B1 to DeLuca disclose a calcium formate composition for oral administration to an individual for the purpose of inhibiting gastrointestinal absorption of phosphorus. It further discloses a method of inhibiting gastrointestinal absorption of phosphorus, comprising administering orally the composition, preferably close in time to food and beverage consumption. Further, DeLuca discloses a method of inhibiting gastrointestinal absorption of phosphorus, comprising administering orally the calcium formate composition of his invention, preferably close in time to food and beverage consumption.

U.S. Pat. No. 6,887,897 B2 (Walsdorf et al.) discloses a calcium glutarate supplement and its use for controlling phosphate retention in patients on dialysis and suffering from renal failure and associate hyperphosphatemia. Therapeutic benefit can be realized by administering a calcium glutarate compound orally to a patient to increase available calcium and contact and bind with ingested phosphorus in the patient's digestive tract, and thereby prevent its intestinal absorption.

In U.S. Pat. No. 6,926,912 B1 Roberts et al. disclose a non-aluminum containing mixed metal compound or sulphated metal compound useful as phosphate binders in the treatment of hyperphosphatemia. The mixed metal compounds include a mixed metal hydroxyl carbonate containing magnesium and iron and may have a hydrocalcite structure, preferably a non-aged hydrocalcite structure. The phosphate binders disclosed by Roberts et al. have a phosphate binding capacity of at least 30% by weight, based on test methods described in the specification.

In U.S. Pat. No. 7,517,402 B2 Muhammad discloses a phosphate binder, a composition, and a kit, as well as a process for preparing the binder and composition. The binder is characterized as having calcium silicate sites which are connected the one with the other by alumina-silica phosphate bonds.

Ingestion of each of the conventional calcium-containing phosphate binders listed above causes the subject to experience significant side effects. Ingestion of calcium carbonate, for example, causes side effects that include distaste, nausea, flatulence, and constipation. Similarly, ingestion of calcium acetate causes side effects that include distaste, nausea, regurgitation of acetic acid, and constipation. Ingestion of calcium formate causes side effects that include distaste, nausea, albuminuria, and constipation. Ingestion of mixed metal or sulphated compounds having calcium silicate sites which are connected by alumina-silica bonds causes side effects that include absorption of aluminum from the composition and constipation. Side effects reduce patient compliance with dosage regimens.

SUMMARY OF THE INVENTION

The present invention is an oral composition for use in the treatment of hyperphosphatemia comprising a phosphate-binder composition and a stool softener. The present invention provides therapeutic compositions and methods for preventing absorption of phosphate from the gastrointestinal tract of a mammalian subject and reducing the serum phosphorus concentration in said subject. The compositions and methods of the invention provide unique attributes including efficient phosphate binding in the gastrointestinal tract, patient tolerability, and reduced side effects, including the prevention and treatment of constipation using stool softeners that do not irritate the intestine. Thus, the present invention provides phosphate-binding compositions that are safer and more effective for a subject requiring such treatment.

In one aspect, the present invention provides an oral composition suitable for treating hyperphosphatemia comprising a first quantity of a calcium succinate composition and a second quantity of a stool softener. In some embodiments, the oral composition comprises a first therapeutically effective dose of a calcium succinate composition and a second therapeutically effective dose of a stool softener, wherein said stool softener acts as a surfactant, lubricant, or hydrating agent that prevents or treats constipation without irritating the cells lining the intestine. Moreover, oral compositions of the invention may be manufactured using conventional commercial equipment.

Inventive compositions according to the invention can be formulated for oral administration. In some embodiments, inventive compositions are formulated as a nutritional supplement. In some embodiments, inventive compositions of the invention can be in the form of a solution or a suspension, a tablet, a sachet, a hard gelatin capsule, a soft gelatin capsule, a non-gelatin capsule, a lozenge, bead, or chewable gel.

A pharmaceutical composition useful for treating hyperphosphatemia in a warm-blooded animal and reducing the risk of side effects is also disclosed. The compositions and methods of the invention provide unique attributes including efficient phosphate binding, high patient tolerability, and reduced side effects including the prevention or treatment of constipation without irritating the cells lining the intestine or increasing the risk or incidence of diarrhea.

The present invention further provides methods of treating hyperphosphatemia by administering to a subject in need of treatment any one of the compositions described herein. Said methods prevent phosphate absorption from the gastrointestinal tract in a warm-blooded animal, thereby reducing serum phosphorus levels in the animal.

DETAILED DESCRIPTION OF THE INVENTION

Figure 1:
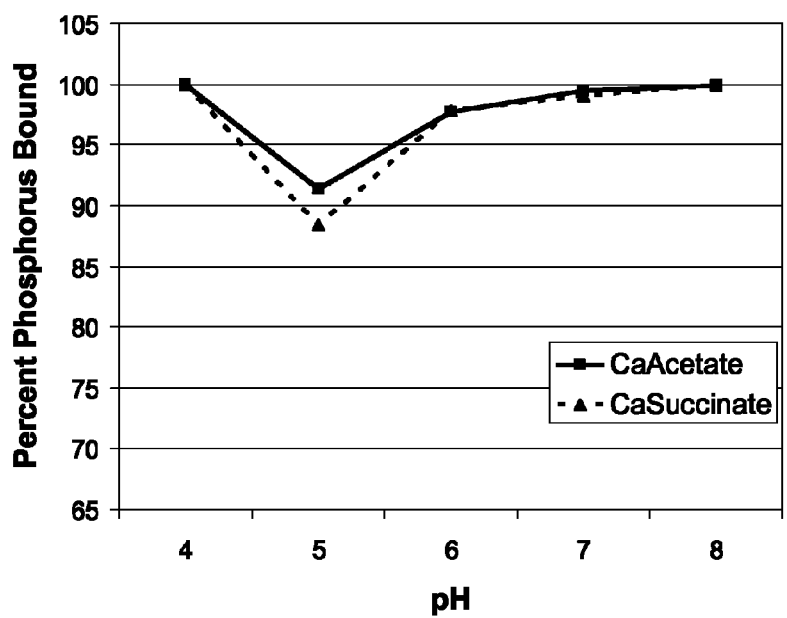
FIG. 1 is a graph comparing the percentage of phosphate bound by a phosphate binder of the invention and a conventional phosphate binder, calcium acetate, in the pH range from pH 4 (the pH of the stomach with food present) to pH 8 (the pH of the lower intestine).

The present invention is an oral composition for use in the treatment of hyperphosphatemia comprising a phosphate-binder composition and a stool softener. In one aspect, the present invention provides an oral composition suitable for treating hyperphosphatemia comprising a first quantity of a calcium succinate composition and a second quantity of a stool softener. In some embodiments, the oral composition comprises a first therapeutically effective dose of a calcium succinate composition and a second therapeutically effective dose of a stool softener, wherein said stool softener acts as a surfactant, lubricant, or hydrating agent that prevents or treats constipation without irritating the cells in the intestinal lumen or increasing the risk or incidence of diarrhea. Preferably, a unit dose of a composition of the invention contains between about 0.45 and 15 g of calcium succinate (i.e., between about 3 and 100 millimoles of calcium as calcium succinate) and a second quantity of a stool softener sufficient to prevent or treat constipation without irritating the cells lining the intestine or increasing the risk or incidence of diarrhea. Compositions of the invention are manufactured using conventional commercial equipment.

Compositions of the invention are administered in a pharmaceutically acceptable oral dosage form (i.e., a solution or a suspension, a tablet, a sachet, a hard gelatin capsule, a soft gelatin capsule, a non-gelatin capsule, a lozenge, bead, or chewable gel, and so forth). In some embodiments, inventive compositions are formulated as a nutritional supplement. In a most preferable embodiment of the present invention, the oral dose is ingested close in time with food and/or beverage consumption (i.e., concurrent with and/or within about 1 hour before or after ingestion of food or beverages).

A pharmaceutical composition useful for treating hyperphosphatemia in a warm-blooded animal and reducing the risk of side effects is also disclosed. The compositions and methods of the invention provide unique attributes including efficient phosphate binding, high patient tolerability, and reduced side effects.

The present invention further provides methods of treating hyperphosphatemia by administering to a subject in need of treatment any one of the compositions described herein. Said methods prevent phosphate absorption from the gastrointestinal tract in a warm-blooded animal, thereby reducing serum phosphorus levels in the animal, and concomitantly prevent or treat constipation without increasing the risk or incidence of diarrhea. Utility of methods of the present invention has been confirmed by demonstrations of effective phosphate-binding without the generation of volatile acids, distasteful acids, and flatulence, or other side effects of conventional preparations.

The term "phosphorus," in defining use of a phosphate-binder composition of the present invention, is intended to embrace both inorganic and organic anions of phosphorus in the various forms that are capable of electrostatic reaction with calcium, including, by way of example, phosphate ($H_2PO_4^{1-}$, $HPO_4^{2-}$, and $PO_4^{3-}$), pyrophosphate ($P_2O_7^{4-}$), and the like.

By the term "calcium succinate composition" is meant calcium succinate (Chemical Abstracts Service Registry No. 140-99-8), a white amorphous powder containing approximately 25% calcium by weight. Calcium succinate has the molecular formula $CaC_4H_4O_4$ and a molecular weight of 156.15. Calcium succinate, which is also named butanedioic acid calcium salt or succinic acid calcium salt, is available commercially (e.g., Jost Chemical Co., St. Louis, Mo.). Also within the scope of this term are hydrates of calcium succinate, succinate salts containing calcium and a second alkali metal ion ($Na^{1+}$, $K^{1+}$, or $Li^{1+}$), crystalline forms of calcium succinate, polymorphic forms of calcium succinate, calcium succinate having specific bulk densities or tap densities, and calcium succinate having specific particle sizes. Calcium succinate compositions are preferred that have particle sizes in ranges that enable complete dissolution of 735 mg of said calcium succinate composition in 900 mL of water at 37° C. within 30 minutes under conditions corresponding to U.S.P. Apparatus II dissolution. Calcium succinate compositions are particularly preferred that particle sizes in ranges that enable at least 80% dissolution of 735 mg of said calcium succinate composition in 900 mL of water at 37° C. within 15 minutes under conditions corresponding to U.S.P. Apparatus II dissolution. Further included within the scope of this term are calcium succinate compositions coated with pharmaceutically acceptable materials intended to modify the release and/or bioavailability of calcium succinate (e.g., Eudragit, microcrystalline cellulose, hydroxypropylmethylcellulose phthalate, and so forth).

The term "calcium" means the calcium ion, $Ca^{2+}$.

A "stool softener" is defined herein as a compound that through its action as a surfactant, lubricant, or hydrating agent prevents or treats constipation without irritating the cells of the intestine. Stool softeners of the invention do not interfere with phosphate binding by calcium succinate compositions or increase the risk or incidence of diarrhea.

The term "excipient material" is intended to mean any compound forming a part of the formulation which is not intended to have biological activity itself and which is added to a formulation to provide specific characteristics to the dosage form, including by way of example, providing protection to the active ingredient from chemical degradation, facilitating release of a tablet or caplet from equipment in which it is formed, and so forth.

By the terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms or conditions.

The phrase "therapeutically effective" is intended to qualify the amount of calcium succinate for use in the orally administered therapy which will achieve the goal of reducing elevated serum phosphorus levels by reducing or inhibiting, for example, the absorption of phosphorus from ingesta in the gastrointestinal tract, while avoiding adverse side effects typically associated with metal-containing phosphorus binding agents.

For the purpose of this disclosure, a warm-blooded animal is a member of the animal kingdom which includes but is not limited to mammals and birds. The most preferred mammal of this invention is human.

For the purpose of this disclosure, dissolution was performed in accordance with U.S. Pharmacopeia (U.S.P.) monograph <711>, Dissolution, Apparatus II (paddles stirred at 50 RPM), using a qualified and calibrated dissolution system. Water (900 mL) maintained at 37° C. was used as the dissolution medium. The rate and extent of release of ionized calcium was monitored.

Surprisingly, the inventor has discovered an oral composition comprising a phosphate-binder composition and a stool softener that provides highly effective phosphate binding in the gastrointestinal tract, tolerability, and reduced side effects, including the prevention and treatment of constipation. Thus, the oral composition of the invention is expected to exhibit improvements in both efficacy and safety as compared to conventional phosphate binders.

Phosphate binding is a chemical reaction between a cation and a phosphorus-containing anion to provide an insoluble phosphate that cannot be absorbed from the gastrointestinal tract. The percentage effectiveness of a phosphate binder may be measured and expressed as the ratio of moles of phosphate-binding agent to moles of phosphate present in the medium multiplied by 100. Ideally, both the cation and the phosphorus-containing anion are in solution, since phosphate-binding is most effective under these conditions. In vivo, effective phosphate-binding is in the range 90% to over 100%; in other words, phosphate binding prevents uptake from the gastrointestinal tract of about 90% to over 100% of the phosphorus-containing anions in the diet. If the phosphorus-containing anion reacts by binding to a partially soluble cation or if the cation is only partially ionized, phosphate-binding will be in the range less than 90%. Thus, it is known that ionized calcium exhibits 90% to 107% effectiveness of phosphate-binding in vivo, whereas lanthanum and sevelamer exhibit about 65% and about 50% phosphate-binding effectiveness in vivo. [Daugircias J T, Finn W F, Emmett M, Chertow G M, et al. The phosphate binder equivalent dose. Seminars in Dialysis (January-February) 2011; 24: 41-49.] For convenience, the effectiveness of phosphate-binding may be measured in vitro by determining percentage of ionized calcium released upon dissolution of a calcium salt composition.

The safety of a phosphate binder is generally described by determination of its biocompatibility (i.e., its ability to be metabolized by the body) and its side effects. Ingestion of any of the conventional phosphate binders listed above causes the subject to experience significant side effects. Ingestion of calcium carbonate, for example, causes side effects that include distaste, nausea, flatulence, and constipation. Similarly, ingestion of calcium acetate causes side effects that include distaste, nausea, regurgitation of acetic acid, respiratory irritation and cough, and constipation. Ingestion of calcium formate causes side effects that include distaste, nausea, albuminuria, and constipation. Ingestion of mixed metal or sulphated compounds having calcium silicate sites which are connected by alumina-silica bonds causes side effects that include absorption of aluminum from the composition and constipation. Side effects reduce patient compliance with dosage regimens. Therefore, a phosphate binder that is not distasteful and does not cause flatulence, formation of a volatile acid, or constipation will be more tolerable to the subject. Likewise, a phosphate binder that is metabolized by the body and does not cause side effects such as the ones described above will be safer for the subject.

The inventor has discovered a calcium succinate composition that provides unexpectedly effective phosphorus binding action as compared to conventional phosphate binders used by a subject requiring treatment for hyperphosphatemia and does not cause many of the side effects characteristic of conventional calcium-containing phosphate binders. While not wishing to be bound by any particular hypothesis or theory, the inventor believes that five factors support using a calcium succinate composition as a phosphorus binder: (1) The solubility and ionization in water of a calcium succinate composition. (2) Weight percent calcium in calcium succinate. (3) Ability of the calcium in a calcium succinate composition to form phosphate salts having reduced bioavailability for absorption from the GI tract. (4) Safety. (5) Low risk for side effects. These factors are discussed in greater detail below.

Solubility and Ionization in Water.

Ionized calcium in solution is the reactive species in Pi binders. Therefore, good solubility and extensive ionization in water are important selection criteria. Calcium succinate has a solubility of 1.28 g/100 mL in water at room temperature. [Dean J A. *Lange's Handbook of Chemistry*. 15$^{th}$ Ed. New York: McGraw-Hill, Inc. 1999.] Preliminary studies by the inventor have shown that its solubility increases by at least two-fold in simulated gastric fluid (0.1 N hydrochloric acid). The experiments disclosed in Example 1 show that calcium succinate is essentially completely ionized in aqueous solution. Thus, all of the calcium ion provided by a calcium succinate composition is available for phosphorus binding and as a result, the effectiveness of phosphate binding in vivo is expected to be quantitative (i.e., greater than 90%).

Weight Percent Calcium in the Salt.

The dose of calcium salt that must be ingested is directly related to the weight percent of calcium that is present in the salt. Calcium comprises 25% of the mass of calcium succinate. This percentage calcium exceeds that of calcium acetate (23%) and other calcium carboxylates that have been used or studied as Pi binders in the past (Table 1, above). Thus, lower doses of calcium succinate provide phosphorus-binding activity equivalent to the activity of calcium acetate and other calcium carboxylates shown in Table 1.

Ability to Form Phosphate Salts Having Reduced Systemic Bioavailability.

In Example 1, the inventor presents theoretical calculations which indicate that ionized calcium from calcium succinate will react readily and nearly quantitatively with Pi in the GI tract to form insoluble and unabsorbable calcium phosphates by the calcium phosphate precipitation reactions that are known to reduce absorption of phosphorus from the gastrointestinal tract. In addition, Marković, Fowler, and colleagues have studied bone formation in vivo and have reported that octacalcium phosphate carboxylates (OCPCs) are formed by a mechanism that applies specifically to succinate salts but not to acetate, carbonate, or citrate salts. [MarkovićM, Fowler B O, Brown W E. Chem Mater 1993; 5: 1401-1405. MarkovićM, Fowler B O, Brown W E. J Cryst Growth 1994; 135: 533-538.] The inventor has discovered that this mechanism comprises yet another reaction by which calcium succinate, but not calcium acetate, calcium carbonate, or calcium citrate, acts as a Pi binder.

The inventor has confirmed the phosphate-binding ability of calcium succinate by studying the phosphorus binding activity of calcium succinate in the pH range from about pH 4 (the pH of the stomach when food is present) to about pH 8 (the pH of the large intestine). Using the experimental conditions presented in detail in Example 1, the inventor has determined the extent of phosphorus binding at each value of solution pH and has found that the extent of phosphorus binding ranges from greater than 90% phosphorus bound at pH 4 to 100% phosphorus bound at pH 8.

Safety.

Hyperphosphatemic subjects (i.e., subjects exhibiting abnormally elevated serum phosphorus levels) may ingest gram doses of Pi binders three or more times each day for many years. Thus, long-term safety is a critical factor in selecting a suitable Pi binder. Succinate is one of several dicarboxylic acids that are intermediates in the citric acid cycle. Therefore, calcium succinate is likely to be biocompatible. Succinate is tasteless and odorless, different from acetate and formate, which have pungent and objectionable odors. Acetate causes regurgitation of acetic acid (vinegar breath) as well as gastric and esophageal irritation following ingestion by a subject. Formate is reported in the Merck Index [*The Merck Index*, 13*th* Edition, Rahway, N.J.] to be a cause of albuminuria or hematuria and a strong irritant; succinate is not. Moreover, succinate is an intermediate in the tricarboxylic acid cycle and is efficiently metabolized by mammals.

Low Risk of Side Effects.

Since large doses of the commonly used calcium carbonate and calcium acetate salts are required with each meal for optimal effectiveness, their side effects—distaste during ingestion and the constipation that often ensues later—may produce poor medication compliance; therefore, Pi control may remain suboptimal for patients. Other possible side effects of calcium carbonate and calcium acetate include gas, bloating, and headache, and increase in severity with dose. Calcium carbonate is poorly soluble in slightly acidic or near-neutral solutions, and the fact that gastric acid secretion is often impaired in hyperphosphatemic patients may limit its dissolution and ionization [Gold C H, Morley J E, Viljoen M. et al. Nephron 1980; 25:92-95. Hardy P, Sechet A, Hottelart C. et al. Artif Organs 1988; 22: 569-573. Tan C C, Harden P N, Rodger R S. et al. Nephrol Dial Transplant 1996; 11:851-853.] In addition, improperly sourced or poorly formulated calcium carbonate tablets may fail to dissolve, further limiting calcium availability in unpredictable ways. Calcium acetate is poorly tolerated, and distaste, "acetic acid breath" ("vinegar breath"), and discomfort have been reported to reduce patient compliance. Hypercalcemia has been observed in CKD patients using both calcium acetate and calcium carbonate. [Meric F, Yap P, Bia M J. Am J Kidney Dis 1990; 16: 459-464.] Epidemiologic studies show strong independent correlations between risk of death and either hyperphosphatemia or a high calcium-phosphorus product (i.e., [Ca, mg/dL]×[P, mg/dL]).

By comparison to either calcium carbonate or calcium acetate, calcium succinate exhibits low risk for side effects. Calcium succinate does not cause gas, acid regurgitation, gastric and esophageal irritation, or other in vivo side effects caused by conventional calcium salts.

Conventional treatments for constipation include foods, bulk-producing compounds or drugs taken to ease movement of feces along the colon by retention of intraluminal fluid through hydrophilic or osmotic mechanisms; decreased net absorption of fluid by effects on small and large bowel fluid and electrolyte transport; or effects on motility by either inhibiting nonpropulsive contractions or stimulating propulsive contractions. Table 2 summarizes effects on bowel function of exemplary conventional agents used to treat constipation.

TABLE 2

Summary of effects of exemplary conventional agents used to treat constipation*

| | Small Bowel | | Colon | | |
|---|---|---|---|---|---|
| Agent | Transit Time | Mixing Contractions | Propulsive Contractions | Mass Actions | Stool Water |
| Dietary fiber | ↓ | ? | ↑ | ? | ↑ |
| Magnesium | ↓ | — | ↑ | ↑ | ↑↑ |
| Lactulose | ↓ | ? | ? | ? | ↑↑ |
| Docusates | ↓ | ? | ? | ? | — |
| Poly(ethylene glycols) (PEGs) | ↓ | ? | ? | ? | ↑↑ |
| Poloxamers | ↓ | ? | ? | ? | ↑↑ |
| Anthraquinones | ↓ | ↓ | ↑ | ↑ | ↑↑ |
| Diphenylmethanes | ↓ | ↓ | ↑ | ↑ | ↑↑ |
| Metoclopramide | ↓ | ? | ↑ | ? | — |
| Cisapride | ↓ | ? | ↑ | ? | ↑ |
| Erythromycin | ↓ | ? | ? | ? | ? |
| Naloxone | ↓ | ↓ | — | — | ↑ |

*Key: "↑" = increased; "↓" = decreased; "?" = available data vary with specific agent and are not easily summarized here; "—" = no effect on this parameter; italicized agent = drug substance having other significant effects on health and well-being.

A hyperphosphatemic subject may suffer from a number of co-morbidities, including hypertension, chronic kidney disease, diabetes, or cancer. As a result, a hyperphosphatemic subject may ingest numerous drugs each day to treat both hyperphosphatemia and any co-morbidities. If the hyperphosphatemic subject now adds a conventional agent for treatment of constipation to the drugs required for treatment of hyperphosphatemia and existing co-morbidities, this action adds to the number of "pills" that must be ingested by the subject (i.e., the "pill burden" of the subject). Further, the inventor has discovered that a conventional agent that is arbitrarily selected by a hyperphosphatemic subject may subsequently interfere with phosphate binding by a composition of the invention.

For example, as disclosed in Examples 2 and 3, the inventor has discovered that conventional agents used to treat constipation such as sodium phosphates, magnesium citrate, magnesium hydroxides (e.g., Milk of Magnesia), or magnesium sulfate interfere with phosphate binding by calcium succinate compositions of the invention. Further, magnesium salts such as those disclosed above are known as "laxatives" that act by irritating the cells lining the intestine. Since the subject being treated for hyperphosphatemia may suffer from inflammation of the intestine, addition of an irritant to prevent or treat constipation may add to the side effects experienced by the subject.

Likewise, the inventor has discovered that lubricants such as mineral oil interfere with phosphate binding by calcium succinate compositions of the invention.

Modern commercial processing equipment must be capable of producing up to a thousand capsules or related oral dosage forms per minute. Through manufacturing carried out at pilot scales using such equipment, the inventor has discovered that poly(ethylene glycol) hyperosmotic agents that are used to prevent or treat constipation interfere with manufacture of phosphate-binding compositions of the invention by clogging the auger used to deliver the formulation during encapsulation. Clogging prevented production at the required rate for commercialization. This discovery indicated that poly(ethylene glycols) are not suitable for use as stool softeners of the invention.

Finally, the inventor has discovered that stool softeners which are surfactants or hyperosmotic agents other than poly(ethylene glycols) do not interfere with phosphate binding by calcium succinate compositions of the invention and do not interfere with manufacture of phosphate-binding compositions of the invention. (These discoveries are summarized in Table 3.)

TABLE 3

Inventor's Discoveries Concerning Treatments for Constipation

| Treatment for Constipation | Interference with phosphate binding | Interference with manufacture of compositions of the invention |
|---|---|---|
| Osmotic agents (e.g., sodium phosphates, magnesium sulfate, magnesium citrate, Milk of magnesia, other magnesium salts) | Yes | Yes |
| Lubricants (e.g., mineral oil) | Yes | Not tested |
| Stool softeners | | |
| Surfactants (e.g., docusates, poloxamers, lactulose, cyclodextrins) | No | No |
| Poly(ethylene glycols) (PEGs) | No | Yes |

The inventor has embodied these discoveries in compositions comprising a first quantity of a calcium succinate composition and a second quantity of a stool softener. A composition of the invention provides effective phosphate binding, tolerability, safety, and relief from a significant side effect of conventional phosphate binders, constipation. Further, the inventor has discovered compositions comprising a first quantity of a calcium succinate composition and a second quantity of a stool softener that can be manufactured into dosage forms using conventional commercial manufacturing equipment.

Thus, as disclosed in Examples 2 and 3, through a series of experiments, the inventor has discovered stool softeners that do not interfere with the phosphate-binding action of a calcium succinate composition but retain stool softening activity. Thus, the inventor has discovered that stool softeners such as docusate, lactitol, lactulose, and cyclodextrins such as alpha-, beta-, and gamma-cyclodextrin and pharmaceutically acceptable beta-cyclodextrin derivatives provide stool softening action and do not interfere with the release of ionized calcium for phosphate binding by a calcium succinate composition (Example 3). The inventor's experiments (Example 3) have also shown that conventional agents for treatment of constipation that contain prevent release of ionized calcium and reduce the effectiveness of phosphate binding by a calcium succinate composition of the invention. Data concerning each stool softener are available for the skilled practitioner to select a quantity of a stool softener that is sufficient to reduce the incidence of constipation but not sufficient to increase the incidence of diarrhea.

A unit dose of an oral composition of the present invention comprises a first quantity of a calcium succinate composition that provides between about 3 millimoles and about 200 millimoles calcium as calcium succinate and a second quantity of a stool softener in a dose sufficient to reduce the incidence of constipation but not sufficient to increase the incidence of diarrhea. The stool softener is selected from the group consisting of docusate, lactulose, lactitol, alpha-cyclodextrin, beta-cyclodextrin, gamma-cyclodextrin, and a pharmaceutically acceptable beta-cyclodextrin derivative. Based on the recommendations of clinicians, including those published in the article entitled "Recommendations on chronic constipation (including constipation associated with irritable bowel syndrome) treatment" [Canadian Journal of Gastroenterology, volume 21 (Supplement B), pages 3B-22B, 2007] and in the monograph entitled "Systematic review of the effectiveness of laxatives in the elderly" [Health Technology Assessment, volume 1, number 13, pages 1-53], compositions of the invention comprising a first quantity of calcium as calcium succinate and a second quantity of a stool softer selected from the group consisting of docusate, lactitol, and alpha-cyclodextrin are preferred embodiments of the invention. Particularly preferred embodiments of compositions of the invention comprise a first quantity of calcium as a calcium succinate composition and a second quantity of docusate.

DOSAGE FORMS. The pharmaceutical compositions of this invention can be administered by any means that effects contact of the therapeutically active ingredients (i.e., active ingredients) with the site of action in the body of a warm-blooded animal. A most preferred administration is by the oral route (i.e., ingestion). The active ingredients can be administered by the oral route in solid dosage forms, such as tablets, capsules, and powders, or in liquid dosage forms, such as solutions, elixirs, syrups, and suspensions. If the active ingredients are administered in a solid dosage form using a hard gelatin capsule, the extent of dissolution and release of ionized calcium is reduced by storage at temperatures greater than 30° C. Therefore, if the active ingredients are formulated in a capsule dosage form, a non-gelatin-containing capsule is preferred. Compositions of the invention are preferably made in the form of a dosage unit containing a particular amount of each active ingredient.

In general, the pharmaceutical compositions of this invention can be prepared by conventional techniques, as are described in *Remington's Pharmaceutical Sciences*, a standard reference in this field [Gennaro A R, Ed. *Remington: The Science and Practice of Pharmacy*. 20$^{th}$ Edition. Baltimore: Lippincott, Williams & Williams, 2000]. For therapeutic purposes, the active components of this invention are ordinarily combined with one or more excipients appropriate to the indicated route of administration. Such capsules or tablets may contain a controlled-release formulation as may be provided in a dispersion of active compound in hydroxypropyl methylcellulose or related material known to alter the kinetics of release of the active agent. Solid dosage forms can be manufactured as sustained release products to provide for continuous release of medication over a period of hours using known pharmaceutical techniques. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

Serum phosphorus levels rise easily after a large meal. Therefore, dosing for oral administration preferably comprises a regimen calling for administration of a therapeutic dose of an oral composition of the present invention close in time to the ingestion of food and/or beverages. Dosing may be subdivided in a manner in which a portion of the prescribed dose is ingested prior to consumption of food or beverages, another portion is ingested together with food or beverages, and yet other portions are ingested close in time after ingestion of food or beverages. Preferably, dosing occurs within about an hour prior to and after ingestion of food or beverages.

The following examples present data confirming the properties of compositions of the invention and descriptions of therapeutic applications of representative pharmaceutical compositions of the present invention and their anticipated outcomes in treating hyperphosphatemia in subjects requiring such treatment. The examples are representative of the scope of the invention, and as such are not to be considered or construed as limiting the invention recited in the appended claims.

Example 1

In Vitro Assessment of Phosphate Binding by a Calcium Succinate Composition of the Invention Test Preparations:

Solutions of the test article (calcium succinate) and control article (calcium acetate) were prepared in deionized, purified water having 18 MΩ or greater resistance. The pH of each solution was adjusted to the desired value by the addition of concentrated hydrochloric acid or sodium hydroxide, as appropriate.

Tests and Assays:

Calcium succinate was assayed as described in the U.S. Pharmacopeia by dissolving an accurately weighed sample in water containing hydrochloric acid, adding hydroxynapthol blue as an indicator, and titrating to a blue endpoint with edetate disodium solution. An HPLC method with conductivity detection was developed and validated for use in the determination of succinate, acetate and phosphate. The separation was performed on a Dionex AS11 Cation-Exchange HPLC column integrated with an Agilent Series 1100 HPLC system, and detection of the anionic species was enabled using a Dionex ED50 Electrochemical Detector, operating in Conductivity Mode. Limits of Detection and Quantitation were enhanced through the use of a Dionex Anion Self-Regenerating Suppressor. After assay-specific development and verification of assay performance were completed, the analysis of phosphate and succinate or acetate was performed by sampling the test solution and diluting it, if necessary, to a concentration within the linear range of the Assay. The sample was then injected onto the HPLC column and eluted with a sodium hydroxide gradient. Data were acquired using Agilent ChemStation® software.

Experimental Methods:

Experiments were completed in triplicate in which 2.77 g of $Na_2HPO_4 \cdot 7H_2O$ (equivalent to 320 mg of elemental phosphorus) was dissolved in 570 mL of deionized water. The test or control binder was dissolved in deionized water to a volume of 30 mL. The binder solution was added to the phosphorus solution to give a final volume of 600 mL. For each binder study, the phosphorus solutions were titrated by addition of dilute HCl or dilute NaOH to five different initial pH levels: 4, 5, 6, 7, and 8. (These solution pH's span the pH range of the gastrointestinal tract.) Then the beakers containing the solutions were covered with plastic wrap and placed on a stir plate that agitated the solution at ~20 cycles per minute overnight. This stirring rate has been selected because in vitro antacid activity at such low stirring rates has been reported to correlate well with in vivo antacid activity in the stomach. Samples for ion chromatographic assay of solution phosphate (Pi) were taken at 24 hours post-mixing (the maximum time available for phosphorus binding that has been reported in related in vivo studies). The decrease in phosphorus concentration from the original concentration in the phosphorus solution to that of the filtrate represents the bound phosphorus.

The experimental data (FIG. 1) demonstrate that Pi binding by calcium acetate, the U.S. standard of care, decreases from 100% at pH 4 to 92% at pH 5 and then increases to 100% as the pH increases to 6, 7, or 8. Pi binding by calcium succinate matches or exceeds the Pi binding activity of calcium acetate at each pH value in the range from pH 4 to 8.

Further, a comparison of the Pi binding exhibited by a calcium succinate composition of the invention with the binding observed for other calcium salts is provided in Table 4.

TABLE 4

Observed in vitro Pi binding for calcium compounds at pH 6

| Calcium Source | % Ca, by weight | Observed in vitro Pi Binding, % | | Comments |
|---|---|---|---|---|
| | | pH 4.0 | pH 6.0 | |
| Calcium Acetate | 23% | 58.6% | 93.8% | Inventor's experiments (Note 1); confirm data of Sheikh et al. (NOTE 2) |
| Calcium Succinate | 25% | 59.4% | 94.0% | Inventor's experiments (Note 1) |
| Calcium Carbonate | 40% | Not Reptd. | 90 | NOTE 2 |
| Calcium Citrate | 21% | Not Reptd. | 10 | 20% at pH 6.5 (NOTE 2) |
| Calcium Formate | 31% | Not Reptd. | Not Reptd. | Not reported. |
| Calcium Lactate | 14% | Not Reptd. | 90 | NOTE 2 |
| Calcium Gluconate | 9.3% | Not Reptd. | 90 | NOTE 2 |

(Note 1): Mean values of triplicate determinations of phosphate and acetate or succinate by anion-exchange HPLC with conductivity detection.
NOTE 2: Sheikh MS, Maguire JA, Emmett M, Santa Ana CA, Nicar MJ, Schiller LR, Fordtran JS. Reduction of dietary phosphorus absorption by phosphorus binders: A theoretical, in vitro, and in vivo study. J Clin Invest 1989; 83: 66-73.

The data in Table 4 confirm that Pi binding by both calcium acetate and calcium succinate occurs at values of pH as low as pH 4.0 but is nearly quantitative at values of pH near neutrality. Note as well that these in vitro data fail to predict the differences in Pi binding by the various calcium salts that are observed in vivo, nor do these in vitro data reveal the poor dissolution of calcium carbonate in the stomach and the "vinegar breath" associated with ingestion of calcium acetate.

Neither of these shortcomings is observed when calcium succinate of the present invention is used as a Pi binder.

Example 2

Phosphate Binding by Calcium Succinate/Stool Softener Compositions

Experimental Methods:

Experiments were completed in 0.1 M borate buffer. Sodium phosphate dibasic heptahydrate ($Na_2HPO_4 \cdot 7H_2O$; 762.12 mg, 2.84 mmol; equivalent to 357 mg of phosphate) was dissolved in 100 mL of 0.1 M borate buffer. One milliliter of the resulting solution was removed and diluted volumetrically to 50 mL with 100 µM KOH solution for determination of the initial phosphate concentration. Calcium succinate monohydrate (681.95 mg, 3.9 mmol Ca) was added as the solid to the stirred phosphate solution to provide "Binding Solution 1." The pH of the resulting solution was determined as 6.26. After Binding Solution 1 was stirred at ambient temperature for 24 hours, 1 mL of the supernatant was removed, filtered, transferred to a 50-mL volumetric flask, and diluted to volume with 100 µM KOH solution for determination of the final phosphate concentration in Binding Solution 1. (A period of 24 hr was selected, because this corresponds to the maximum time available for phosphorus binding that has been reported in related in vivo studies.)

In a second experiment, sodium phosphate dibasic heptahydrate ($Na_2HPO_4 \cdot 7H_2O$; 762.12 mg, 2.84 mmol; equivalent to 357 mg of phosphate) was dissolved in 100 mL of 0.1 M borate buffer. Poly(ethylene glycol) (PEG, average molecular weight 2,000 Daltons; 100 mg) was added, and the solution was stirred until dissolution was complete. One milliliter of the resulting solution was removed and diluted volumetrically to 50 mL with 100 µM KOH solution for determination of initial phosphate concentration. Calcium succinate monohydrate (682.23 mg, 3.9 mmol Ca) was added as the solid to the stirred phosphate/PEG solution to provide "Binding Solution 2" (a binding solution containing a stool softener). The pH of the resulting solution was determined as 6.28. After Binding Solution 2 was stirred for 24 hours, 1 mL of the supernatant was removed, filtered, transferred to a 50-mL volumetric flask, and diluted to volume with 100 µM KOH solution for determination of the final phosphate concentration in Binding Solution 2.

Figure 2:
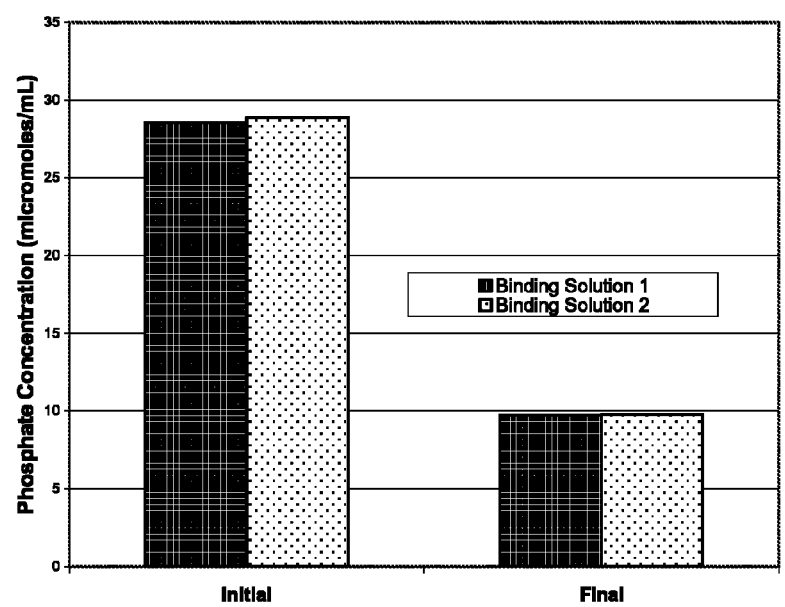
FIG. 2 is a graph comparing the percentage of phosphate bound by a phosphate binder of the invention comprising a calcium succinate composition in the absence or the presence of a stool softener (Binding Solution 1 and Binding Solution 2, respectively). Phosphate was present in excess in the solutions.

Samples were analyzed using a validated ion chromatographic assay of solution phosphate (Pi). The decrease in phosphorus concentration from the original concentration in the phosphorus solution to that of the filtrate represents the bound phosphorus. The experimental data (FIG. 2) demonstrate that Pi binding by a phosphate binder of the invention is identical in the absence (Binding Solution 1) or in the presence (Binding Solution 2) of a stool softener of the invention.

Example 3

Phosphate Binding Effectiveness of Compositions of the Invention

Phosphate binding is a chemical reaction between a cation and a phosphorus-containing anion to provide an insoluble phosphate that cannot be absorbed from the gastrointestinal tract. The percentage effectiveness of a phosphate binder may be measured and expressed as the ratio of moles of phosphate-binding agent to moles of phosphate present in the medium multiplied by 100. Ideally, both the cation and the phosphorus-containing anion are in solution, since phosphate-binding is most effective under these conditions. In vivo, effective phosphate-binding by ionized calcium is in the range 90% to over 100%. For convenience, the effectiveness of phosphate-binding by a calcium salt may be measured in vitro by determining the ionized calcium released by dissolution of a unit dose of a formulation. Therefore, the effectiveness of phosphate binding by experimental formulations of compositions of the invention was determined by monitoring the rate and extent of ionized calcium release into water through dissolution at 37° C.

Test Preparations:

Capsules containing experimental formulations of compositions of the invention (Test Articles) were prepared in the laboratory.

Tests and Assays:

An HPLC method with conductivity detection was developed and validated for use in the determination of calcium. The separation was performed on a Dionex AS11 Cation-Exchange HPLC column integrated with a Dionex HPLC system, and detection of the cationic species was enabled using a Dionex ED50 Electrochemical Detector operating in Conductivity Mode. Limits of Detection and Quantitation were enhanced through the use of a Dionex Cation Self-Regenerating Suppressor. After assay-specific development and verification of assay performance were completed, the analysis of calcium was performed by sampling the test solution and diluting it, if necessary, to a concentration within the linear range of the Assay. The sample was then injected onto the HPLC column and eluted with a gradient of methanesulfonic acid-containing mobile phase. Data were acquired and analyzed using Agilent ChemStation® software.

Experimental Methods:

Experiments were completed in which one unit dose of an experimental composition of the invention was dissolved in 900 mL of deionized water at 37° C. under the dissolution conditions associated with U.S. Pharmacopeia Apparatus II. Twelve unit doses of each experimental composition were tested in this manner. Samples for ion chromatographic assay of ionized calcium were taken at 0, 5, 10, 15, 20, 30, 45, and 60 minutes. Over thirty formulations were tested. Representative experimental data are summarized in Table 5.

TABLE 5

Extent of Release of Ionized Calcium From Formulations

| Expt. No. | Ingredient | Formulation Composition (% w/w) | Capsule Type | Percent Release of Ionized Calcium @ 30 minutes (USP Apparatus II, Water, 37° C.) |
|---|---|---|---|---|
| 1 | Calcium Succinate | 92.4 | Gelatin | Initial: >90% |
|   | Poly(ethylene glycol) (PEG) | 1.3 | | After storage at 45° C. for |
|   | Other excipients | 6.3 | | 1 month: 0% |
| 2 | Calcium succinate | 91.4 | Non-gelatin | 40% |
|   | Magnesium-containing laxative | 0.2 | | |
|   | Other excipients (A) | 8.4 | | |
| 3 | Calcium succinate | 91.4 | Non-gelatin | 56% |
|   | Magnesium-containing laxative | 0.2 | | |
|   | Other excipients (B) | 8.4 | | |
| 4 | Calcium succinate | 91.4 | Non-gelatin | 44% |
|   | Magnesium-containing laxative | 0.2 | | |
|   | Other excipients (C) | 8.4 | | |

TABLE 5-continued

Extent of Release of Ionized Calcium From Formulations

| Expt. No. | Ingredient | Formulation Composition (% w/w) | Capsule Type | Percent Release of Ionized Calcium @ 30 minutes (USP Apparatus II, Water, 37° C.) |
|---|---|---|---|---|
| 5 | Calcium succinate | 91.9 | Non-gelatin | 88% |
|   | Stool softener A | 0.5 |  |  |
|   | Other excipients | 8.6 |  |  |
| 6 | Calcium succinate | 93.5 | Non-gelatin | 98% |
|   | Stool softener B | 0.5 |  |  |
|   | Other excipients | 6.0 |  |  |

Briefly summarized, the data show that under the dissolution conditions used in the study:

(a) Gelatin capsules are less suitable for encapsulation of formulations of compositions of the invention. At the time of manufacture, 100% of the calcium in a formulation is released into water as ionized calcium. However, if the capsules are stored at temperatures exceeding about 30° C. for as short a time as 1 month, 0% of the calcium in the formulation is released into water as ionized calcium.

(b) Non-gelatin-containing capsules allow release into water of more than 90% of the calcium in compositions of the invention within 30 minutes. Moreover, non-gelatin-containing capsules allow release of more than 80% of the calcium in compositions of the invention within 15 minutes (data not shown). Therefore, a preferred embodiment of compositions of the invention is non-gelatin-containing capsules containing formulations of compositions of the invention.

(c) "Stool softeners" containing magnesium prevent the release of ionized calcium from experimental compositions, an action that prevents phosphate-binding by the compositions.

(d) Stool softeners of the invention do not interfere with the rate or extent of release of ionized calcium from compositions of the invention and reaction of ionized calcium with phosphorus-containing anions in the gastrointestinal tract. Therefore, both effective, efficient phosphate binding and stool softening are properties of compositions of the invention.

Example 4

Phosphate Binding by a Composition of the Invention in Humans

In vivo phosphorus binding by a composition of the invention (Test Article) and a placebo (Control Article) will be assessed in 10 healthy human subjects. The Test Article will be formulated to contain 169 mg of calcium as a calcium succinate composition and 4 mg of a stool softener and will be presented as a non-gelatin-containing capsule. Each subject will be studied on three separate test days: a fast day, a day in which placebo (Control Article) is ingested, and a day in which test (Test Article) is administered. The order of testing will be randomized. Net calcium absorption will be measured by a validated method, such as the one described in detail by Bo-Linn, G. W. et al., Journal of Clinical Investigation, 73: 640-647 (1984). The procedure that will be followed is described below.

On each day, subjects will be prepared by a mannitol-electrolyte gastrointestinal lavage, in order to cleanse the gastrointestinal tract.

On one of the test days (the "fast day"), subjects will ingest no meal, placebo or Test Article; the rest of the procedure will be the same.

On the "placebo day," four hours after completion of the washout, subjects will consume 25 mEq. of a placebo (lactose) with 100 mL of deionized water. Then each subject will eat a meal of 80 g ground sirloin steak, 100 g French fried potatoes, 30 g Swiss cheese and 250 mL water containing 10 g of polyethylene glycol (PEG3500) as a non-absorbable marker. [Duplicate meals will be prepared (one for consumption and one to be analyzed for calcium and phosphorus). The duplicate meals will be analyzed for calcium and phosphorus and are expected to contain about 350 mg of phosphorus and about 215 mg of calcium.] After the meal, each subject will consume 25 mEq of placebo with 100 mL of water.

On the "test day," four hours after completion of the washout, subjects will consume 25 mEq. of calcium (as at least one dosage unit of a composition of the invention) with 100 mL of deionized water. Then each subject will eat a meal of 80 g ground sirloin steak, 100 g French fried potatoes, 30 g Swiss cheese and 250 mL water containing 10 g of polyethylene glycol (PEG3500) as a non-absorbable marker. [Duplicate meals will be prepared (one for consumption and one to be analyzed for calcium and phosphorus). The duplicate meals will be analyzed for calcium and phosphorus and are expected to contain about 350 mg of phosphorus and about 215 mg of calcium.] After the meal, each subject will consume 25 mEq of calcium, in the same form as will have been consumed prior to the meal, or additional placebo, with 100 mL of water.

Ten hours after a meal, a second lavage will be begun, using the procedure described above. This will remove unabsorbed material from the gut. All urine voided during the 10-hour period will be collected and analyzed for phosphorus and calcium. Rectal effluent will be collected, pooled with any stool passed during the 10-hour period and analyzed for phosphorus and calcium. Absorption will be calculated according to the following equation:

Net phosphorus(P)absorption=(P content of duplicate meal, mg)−(Total Effluent P, mg)

Net calcium(Ca)absorption=(Ca content of meal, as determined from duplicate meal, mg)+(Ca ingested as Ca succinate, mg)−(Total Effluent Ca, mg)

Experimental results are expected to demonstrate that oral administration of a composition results in the inhibition of phosphorus absorption, when ingested close in time to food and beverage consumption. In other words, it is anticipated that on the placebo day, as much as about 70% or more of the dietary phosphorus will be absorbed from the GI tract of each subject. By comparison, on the day in which a composition of the invention is ingested close in time to food and beverage consumption, it is anticipated that as little as about 20% of dietary phosphorus will be absorbed. In addition, the results are expected to demonstrate that a composition of the invention is an efficient inhibitor of calcium absorption, when ingested close in time to food and beverage consumption. In other words, it is anticipated that on the placebo day, about 20-40% of the dietary calcium will be absorbed from the GI tract of each subject. By comparison, on the day in which a composition of the invention is ingested, it is anticipated that less than about 10% change will be observed in the percentage of the dietary calcium that is absorbed from the GI tract of each subject.

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

I claim:

1. A composition for inhibiting absorption of phosphorus-containing anions from the gastrointestinal tract of a subject consisting of:

a source of ionized calcium, a stool softener, and a non-gelatin capsule, wherein:

a) the source of ionized calcium is a calcium succinate composition, b) the quantity of the calcium succinate composition provides ionized calcium in a quantity sufficient to bind with said phosphorus-containing anions in the gastrointestinal tract of the subject, c) the quantity of said stool softener is sufficient to reduce the incidence of constipation but not sufficient to increase the incidence of diarrhea, d) said stool softener is selected from the group consisting of docusate and lactulose, e) said stool softener does not interfere with the binding of said phosphorus-containing anions by said ionized calcium, f) said stool softener does not interfere with the manufacture of said composition, g) dissolution of the composition in water at 37° C. that is stirred at 50 RPM under the dissolution conditions described in the U.S. Pharmacopeia for Apparatus II releases at least about 80% of the calcium in the composition as ionized calcium in 30 minutes.

2. The composition according to claim 1 wherein a unit dose of said composition provides between 3 and 200 milliequivalents of ionized calcium.

* * * * *